(12) United States Patent
Liu

(10) Patent No.: US 8,709,358 B2
(45) Date of Patent: Apr. 29, 2014

(54) CARTRIDGE FOR SEPARATING ANALYTE FROM MIXTURE, COMPRISING DISPENSING AND RECEIVING CHAMBERS AND INSERT

(75) Inventor: Xiao-Chuan Liu, Upland, CA (US)

(73) Assignee: MaxAffinity LLC, Upland, CA (US)

( * ) Notice: Subject to any disclaimer, the term of this patent is extended or adjusted under 35 U.S.C. 154(b) by 337 days.

(21) Appl. No.: 13/105,736

(22) Filed: May 11, 2011

(65) Prior Publication Data

US 2011/0294224 A1 Dec. 1, 2011

Related U.S. Application Data

(60) Provisional application No. 61/396,328, filed on May 26, 2010.

(51) Int. Cl.
*B01D 21/00* (2006.01)

(52) U.S. Cl.
USPC .............................. 422/527; 436/177; 436/178

(58) Field of Classification Search
None
See application file for complete search history.

(56) References Cited

U.S. PATENT DOCUMENTS

| 6,562,581 B2 | 5/2003 | Law et al. |
| 6,582,964 B1 | 6/2003 | Samsoondar et al. |
| 7,670,853 B2 | 3/2010 | Jina |

OTHER PUBLICATIONS

Herold et al. "Robotic Chromatography: Development and Evaluation of Automated Instrumentation for Assay of Glycohemoglobin", Clin. Chem., 1993, v. 39, No. 1, pp. 143-147.*
Weith, H. L., et al., "Synthesis of Cellulose Derivatives Containing the Dihydroxyboryl Group and a Study of Their Capacity to Form Specific Complexes with Sugars and Nucleic Acid Components," Biochemistry, vol. 9, No. 22, 1970, pp. 4396-4401.
Mallia, A. Krishna, et al., "Preparation and Use of a Boronic Acid Affinity Support for Separation and Quantitation of Glycosylated Hemoglobins," Analytical Letters, 14(B8), 1981, pp. 649-661.
Bisse, E., et al., "Coupling of *m*-aminophenylboronic acid to *s*-triazine-activated Sephacryl: use in the affinity chromatography of glycated hemoglobins," Journal of Chromatography, 575, 1992, pp. 223-228.

* cited by examiner

*Primary Examiner* — Yelena G Gakh
(74) *Attorney, Agent, or Firm* — Christie, Parker & Hale, LLP

(57) ABSTRACT

Devices, systems, and methods for separating an analyte from a mixture, and devices, systems, and methods for measuring an amount of an analyte are disclosed. The devices, systems, and methods may be used to separate glycated hemoglobin from other blood components and to measure the amount of the glycated hemoglobin.

18 Claims, 9 Drawing Sheets

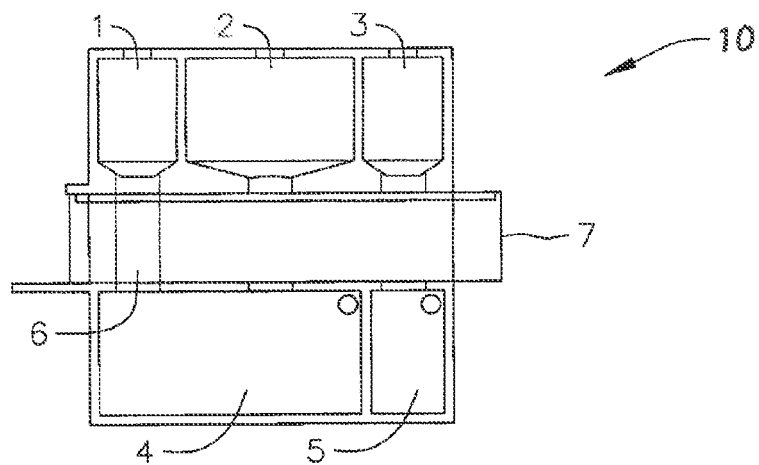
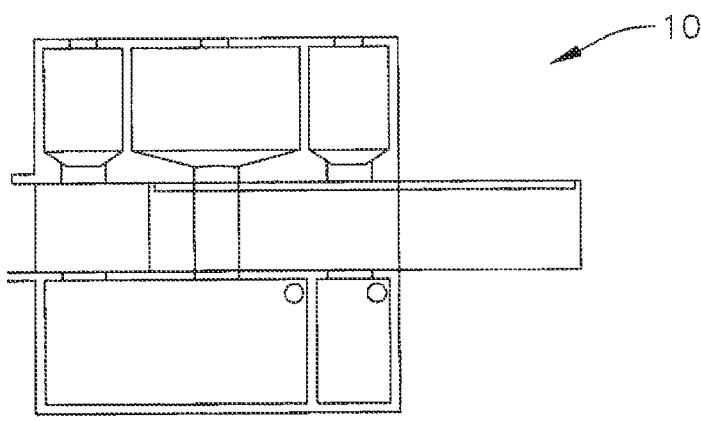
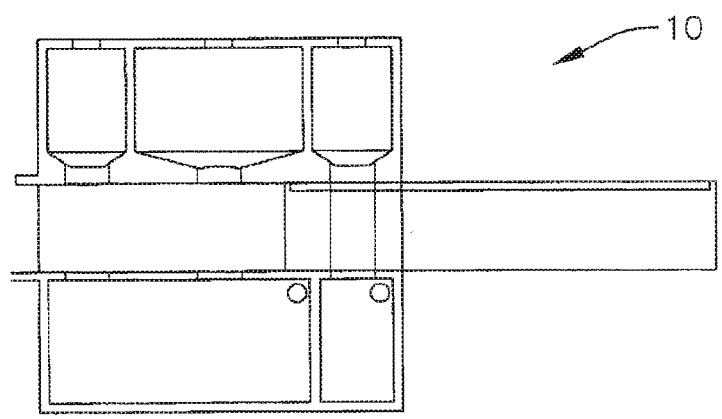

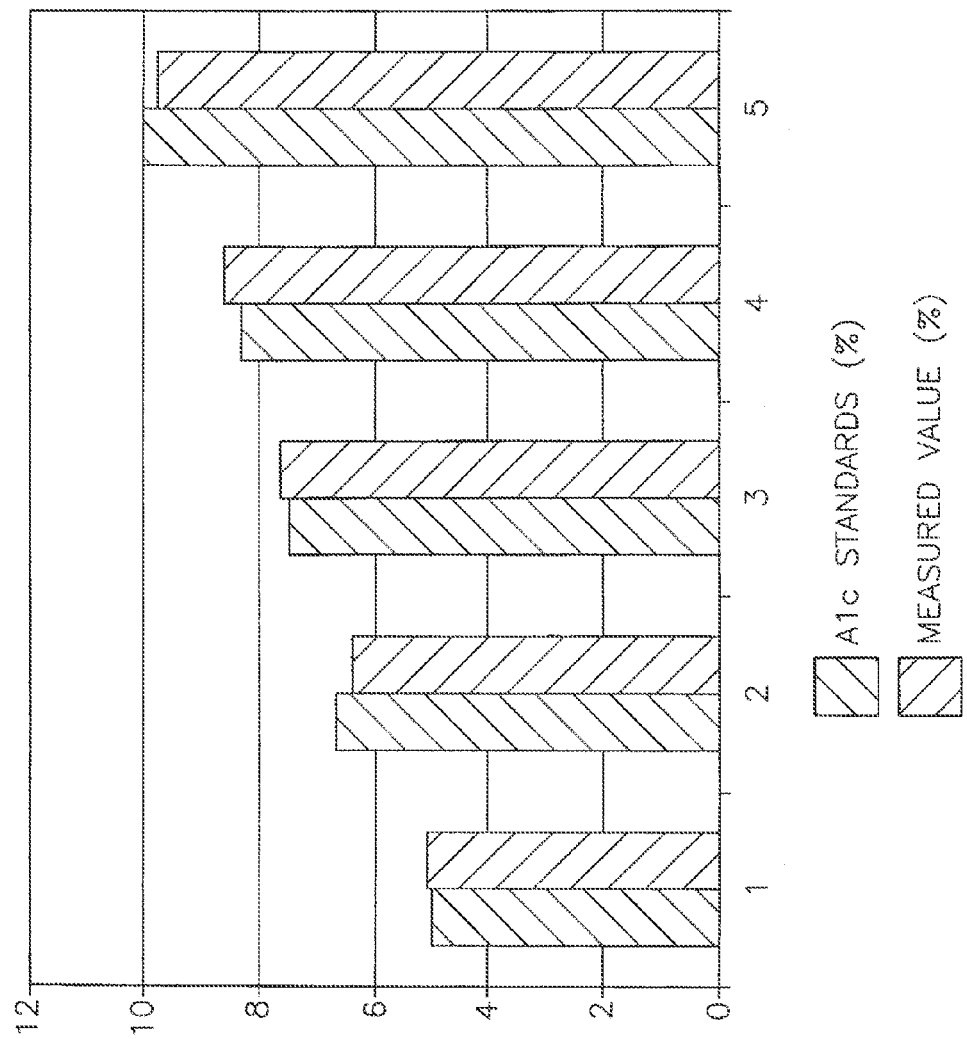

CARTRIDGE FOR SEPARATING ANALYTE FROM MIXTURE, COMPRISING DISPENSING AND RECEIVING CHAMBERS AND INSERT

CROSS-REFERENCE TO RELATED APPLICATION(S)

This application claims priority to and the benefit of U.S. Provisional Application No. 61/396,328, titled "Portable Device for Determination of Glycated Hemoglobin (GHb A1c)," filed on May 26, 2010, the entire content of which is incorporated herein by reference.

FIELD

One or more embodiments of the present invention generally relate to devices, systems, and methods for separating an analyte from a mixture. Embodiments of the present invention further generally relate to devices, systems, and methods for measuring an amount of an analyte. Certain embodiments of the present invention generally relate to devices, systems, and methods for separating glycated hemoglobin from other components of blood. Additionally, embodiments of the present invention generally relate to devices, systems, and methods of measuring an amount of glycated hemoglobin.

BACKGROUND

Diabetes is one of the leading causes of death and disability in the world. There are over 170 million diabetics worldwide. And the number of diabetic patients has increased 11% for the last five years. The World Health Organization estimates there will be 300 million diabetic patients by 2025. Currently there is no cure for the disease. Thus, it is critical for diabetic patients to manage and control their disease.

Measuring the concentration of glycated hemoglobin (hemoglobin A1c or GHb A1c) in a patient's blood may provide an indication of the mean glycemic control during a period of several months prior to the measurement. Diabetes Control and Complications Trial (DCCT) appears to have established a relationship between the measured GHb A1c concentration in a patient's blood and the risks for development and progression of chronic complications of diabetes. Therefore, the American Diabetes Association (ADA) recommends measuring GHb A1c levels in all diabetic patients and recommends specific treatment goals for maintaining particular GHb A1c levels. Additionally, measuring the level of glycated hemoglobin may be especially important for smokers, as the present inventor has recently discovered that nicotine may promote (contribute to) the formation of glycated hemoglobin.

Accordingly, there is a need for a portable device that can quickly and accurately measure the GHb A1c level of a patient's blood in a laboratory, doctor's office, or patient's home.

SUMMARY

Aspects of embodiments of the present invention are directed to a cartridge for separating an analyte from a mixture, the cartridge including: two or more dispensing chambers; two or more receiving chambers adjacent to the dispensing chambers; and an affinity medium positioned between at least one dispensing chamber and at least one receiving chamber, wherein at least one of the dispensing chambers, receiving chambers, or affinity medium is configured to move relative to the others, to allow the affinity medium to be positioned between at least one dispensing chamber and at least one receiving chamber.

According to certain embodiments, the affinity medium is movably positioned between at least one dispensing chamber and at least one receiving chamber.

Additionally, the cartridge may be configured to selectively couple each of the dispensing chambers to the affinity medium according to the position of the affinity medium.

The cartridge may also be configured to selectively couple the affinity medium to each of the receiving chambers according to the position of the affinity medium.

Alternatively, the dispensing chambers may be movably positioned adjacent to the affinity medium.

The receiving chambers may also be movably positioned adjacent to the affinity medium.

According to certain embodiments, the cartridge is configured to selectively couple each of the dispensing chambers to the affinity medium according to the position of each of the dispensing chambers.

Additionally, the cartridge may be configured to selectively couple the affinity medium to each of the receiving chambers according to the position of each of the receiving chambers.

According to certain embodiments, the cartridge further includes at least one dispensing flow path between at least one of the dispensing chambers and the affinity medium.

Additionally, the cartridge may also further include at least one receiving flow path between the affinity medium and at least one of the receiving chambers.

The at least one dispensing flow path may be configured to selectively couple each of the dispensing chambers to the affinity medium.

The at least one receiving flow path may be configured to selectively couple the affinity medium to each of the receiving chambers.

At least one of the dispensing chambers may be configured to dispense a mixture including at least one reagent.

Additionally, the at least one reagent may be configured to lyse human or animal blood cells.

In certain embodiments, the at least one reagent is sodium azide.

At least one of the receiving chambers may be configured to receive an analyte.

The analyte may be glycated hemoglobin (hemoglobin A1c).

According to certain embodiments, the affinity medium includes a polymer including a binding moiety.

The polymer may be cross-linked.

The polymer may include agarose.

The polymer including a binding moiety may be the reaction product of a polymer and a boronic acid.

The polymer may further include a spacer or activator.

Aspects of embodiments of the present invention are also directed to a system including a cartridge for separating an analyte from a mixture, the cartridge including: two or more dispensing chambers; two or more receiving chambers adjacent to the dispensing chambers; and an affinity medium positioned between at least one dispensing chamber and at least one receiving chamber, wherein the system is configured to measure the amount of the analyte.

The system may further include a spectrometer.

Aspects of embodiments of the present invention are also directed to a method of measuring the amount of an analyte, the method including: separating the analyte from a mixture using an affinity medium and spectroscopically measuring the amount of the analyte.

In certain embodiments the method of measuring the amount of an analyte includes: selectively coupling a first dispensing chamber to an affinity medium to allow a first reagent and a mixture including the analyte to flow past the affinity medium, thereby binding the analyte to the affinity medium; selectively coupling the affinity medium to a first receiving chamber to allow the residual first reagent and mixture to flow into the first receiving chamber; selectively coupling a second dispensing chamber to the affinity medium to allow a second reagent to flow past the affinity medium and bound analyte, thereby washing the affinity medium and bound analyte; selectively coupling the affinity medium to the first receiving chamber to allow the residual second reagent to flow into the first receiving chamber; selectively coupling a third dispensing chamber to the affinity medium to allow a third reagent to flow past the affinity medium, thereby releasing the bound analyte; selectively coupling the affinity medium to a second receiving chamber to allow the residual third reagent and analyte to flow into the second receiving chamber; and spectroscopically measuring the amount of the analyte, wherein the first, second, and third reagents are the same or different.

In certain embodiments, the method of measuring the amount of the analyte includes separating glycated hemoglobin from non-glycated hemoglobin, spectroscopically measuring the amount of glycated hemoglobin, and spectroscopically measuring the amount of non-glycated hemoglobin.

BRIEF DESCRIPTION OF THE DRAWINGS

The accompanying drawings, together with the specification, illustrate exemplary embodiments of the present invention, and, together with the description, serve to explain the principles of the present invention.

FIGS. 3A-3C are side views of a cartridge showing operation of the cartridge according to exemplary embodiments of the present invention.

FIG. 9 is a graph of the glycated hemoglobin (GHb A1c) concentration for a series of standard samples; the reported concentrations and concentrations measured according to a system and method of exemplary embodiments of the present invention are shown.

DETAILED DESCRIPTION

Figure 1:
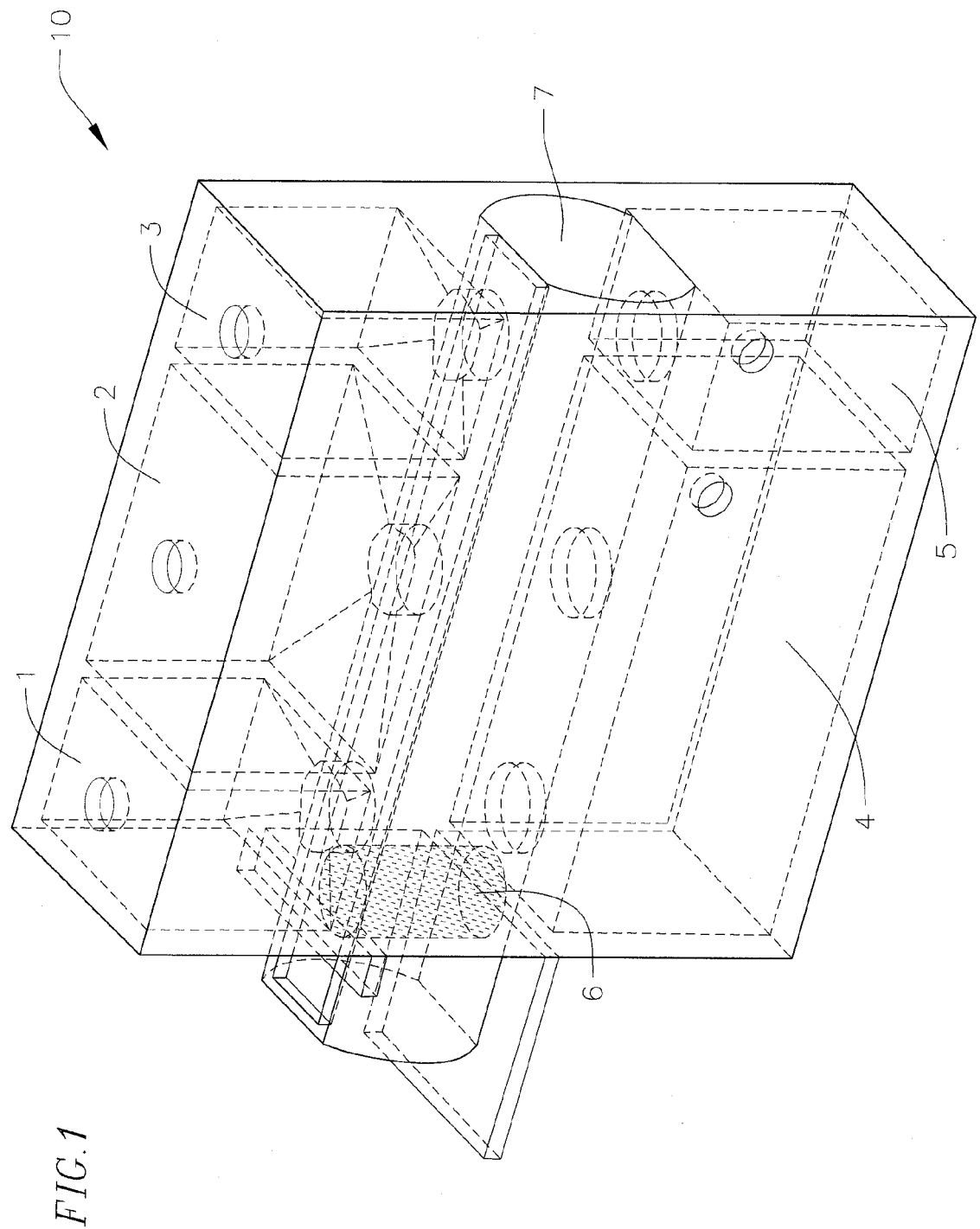
FIG. 1 is an axonometric view of a cartridge according to exemplary embodiments of the present invention.

In the following detailed description, only certain exemplary embodiments of the present invention are shown and described, by way of illustration. As those skilled in the art would recognize, the invention may be embodied in many different forms and should not be construed as being limited to the embodiments set forth herein.

Embodiments of the present invention generally relate to a cartridge for separating an analyte from a mixture. For example, in certain embodiments, the cartridge is used to separate an analyte from other components of human or animal blood (e.g., whole or modified blood). In particular, the cartridge may be used to separate an analyte including glycated hemoglobin (hemoglobin A1c or GHb A1c) from a mixture including human blood. Embodiments of the present invention rely on the principles of molecular recognition and affinity chromatography. For example, the cartridge may separate the analyte from the mixture by way of affinity chromatography.

Certain embodiments of the present invention also provide a system for measuring an amount of the analyte. The system may include a cartridge according to certain embodiments of the invention. The cartridge may be used to separate the analyte, such as, for example, hemoglobin A1c, from the mixture, such as, for example, human blood, and the system may be used to measure the amount of the separated analyte. Additionally, embodiments of the present invention also relate generally to methods of using the cartridge and the system, either independently or together.

The system according to embodiments of the present invention is highly sensitive. In certain embodiments, as little as 0.2 microliter of blood may be effective, and as little as 10 microliter of affinity medium may be effective. The affinity medium and reagents also have good stability for long shelf-life for a commercial product. The system is small, portable, and can be used in labs, doctor's offices, and (diabetic patients') homes.

In certain embodiments, the cartridge includes two or more dispensing chambers, two or more receiving chambers adjacent to the dispensing chambers, and an affinity medium positioned between at least one dispensing chamber and at least one receiving chamber.

Dispensing Chambers

According to embodiments of the present invention, the cartridge includes at least one dispensing chamber that is configured to receive an analyte containing fluid, such as human or animal blood, and to dispense a mixture including human or animal blood (e.g., whole or modified blood). The mixture may further include at least one reagent. For example, in certain exemplary embodiments, the cartridge includes a first dispensing chamber configured to dispense a mixture including human or animal blood (e.g., whole or modified blood) and at least one first reagent, a second dispensing chamber configured to dispense at least one second reagent, and a third dispensing chamber configured to dispense at least one third reagent. The cartridge may also include additional dispensing chambers. Additionally, the materials dispensed by the dispensing chambers may be varied.

The first, second, and third reagents may be the same or different. For example, in certain embodiments, the first reagent includes at least one chemical compound suitable to lyse the blood cells of the blood to release glycated hemoglobin and/or non-glycated hemoglobin, the second reagent includes at least one chemical compound suitable to wash the affinity medium after the glycated hemoglobin has been bound to the affinity medium, and the third reagent includes at least one chemical compound suitable to release (e.g., liberate) the glycated hemoglobin from the affinity medium thereby allowing the glycated hemoglobin to substantially flow away from the affinity medium.

Each of the dispensing chambers may dispense the materials contained therein by any suitable mechanism. For example, any of the dispensing chambers may dispense the materials contained therein by harnessing the force of gravity. Alternatively, any of the dispensing chambers may dispense the materials contained therein by harnessing a (positive or negative) pressure gradient. For example, any of the dispensing chambers may dispense the material contained therein by applying positive pressure, by way of a gas or liquid, to the material contained in the dispensing chamber. Conversely, any of the dispensing chambers may dispense the material contained therein by applying a negative pressure, by way of a vacuum, to the material contained in the dispensing chamber. As another alternative, any of the dispensing chambers may dispense the materials contained therein by harnessing a mechanical force (e.g., a force applied by a piston, plunger, or the like).

Each of the dispensing chambers may include at least one aperture. For example, each dispensing chamber may have a dispensing aperture configured to dispense the material contained in the dispensing chamber. The dispensing aperture may be positioned at any suitable location in, on, or of the dispensing chamber, for example, at the side of the dispensing chamber adjacent to the affinity medium. Each dispensing chamber may include a filling aperture for filling the dispensing chamber with at least one reagent and/or a mixture including blood. The filling aperture may be located at any suitable location in, on, or of the dispensing chamber, for example, at the top of the dispensing chamber or at the side of the chamber opposite to the affinity medium. The filling aperture may include a seal (or partial seal) to prevent the contents of the dispensing chamber (e.g., the mixture including blood) from escaping the dispensing chamber through the filling aperture. Such a seal may be necessary to prevent the escape of biohazardous materials (e.g., blood). Alternatively, certain dispensing chambers may be pre-filled and then permanently sealed to form a dispensing chamber not having a filling aperture (i.e., only having a dispensing aperture). The dispensing chambers may also include venting apertures for venting the dispensing chambers, as necessary.

Each of the dispensing chambers may be formed of any suitable material. For example, any of the dispensing chambers may be formed of glass, plastic or quartz. The present invention is not particularly limited by the materials of the dispensing chambers.

Each of the dispensing chambers may have any suitable shape, such as any regular or irregular three-dimensional shape. For example, each dispensing chamber may have a cylindrical, cuboid (e.g., a cube or right cuboid), or any other polyhedral shape. The present invention is not particularly limited by the shapes of the dispensing chambers.

Affinity Medium

The affinity medium may include any material suitable for affinity chromatogaphy. For example, embodiments of the present invention may include any of the materials described in U.S. Pat. No. 4,269,605; U.S. Patent Application Publication No. 2002/0172992 A1; H. L. Keith et al., *Biochemistry*, 9, 397-4401 (1970); A. K. Mallia et al., *Analytical Letters,* 14, 649-661 (1981); E. Bisse et al., *Journal of Chromatography: Biomedical Applications,* 575, 223-228, (1992); the entire contents of each of which are herein incorporated by reference.

In certain embodiments, the affinity medium includes a polymer including a binding moiety. The polymer may include any polymer suitable for use as an immobile phase. For example, the polymer may include agarose (e.g., Sepharose™), Sephacryl, or cellulose (e.g., N-(m-dihydroxyborylphenyl)carbamylmethylcellulose and N—[N'-(m-dihydroxyborylphenyl)succinamyl]aminoethylcellulose. The polymer may be cross-linked. The binding moiety may include any suitable boron containing ligand, such as a boronic acid or its derivative. Those of ordinary skill in the art will understand that the term "a boronic acid or its derivative" includes any alkyl or aryl substituted boric acid. In certain embodiments, the binding moiety includes m-aminophenylboronic acid or its derivative. The affinity medium may also include suitable spacers or activators, such as any oxirane-containing organohalide with 3-10 carbon atoms. The spacers and activators may be used to couple the binding moiety to the affinity medium support (e.g., the polymer).

In certain embodiments, the polymer is the reaction product of a polymer (e.g., a polymer including spacers or activators) and a precursor of a binding moiety, such as, for example, any suitable boron containing precursor (e.g., a boronic acid or its derivative). Alternatively, the polymer may be the reaction product of monomers or oligomers and a precursor of a binding moiety, such as, for example, any suitable boron containing precursor (e.g., a boronic acid or its derivative). In other embodiments, the binding moiety of the polymer may be formed via a templating reaction. The polymer may be cross-linked before or after the binding moiety is formed.

According to embodiments of the present invention, the affinity medium is configured to preferentially, and reversibly, bind the analyte to be separated. Specifically, the binding moiety of the affinity medium may be configured to preferentially, and reversibly, bind the analyte to be separated. For example, flowing a mixture, including the analyte to be separated, past the affinity medium may result in the analyte being preferentially, and reversibly, bound to the affinity medium, resulting in the analyte being reversibly retained on, in, around, or adjacent to the affinity medium, while the other components of the mixture are capable of substantially flowing away from the medium. A suitable reagent (e.g., the third reagent) may then be flowed past the affinity medium to release (or liberate) the reversibly bound analyte, thereby allowing the analyte to flow substantially away from the affinity medium.

In exemplary embodiments, the affinity medium is an immobile phase that includes the reaction product of a polymer (or monomers or oligomers) and a boron-containing precursor of a binding moiety. According to those embodiments, the affinity medium includes a boron-containing binding moiety. For example, the affinity medium may include a boron-containing binding moiety formed from sodium borohydride. When a mixture containing an analyte is flowed past the affinity medium, the boron-containing binding moiety may preferentially, and reversibly, bind the analyte to be separated, while allowing the other components of the mixture to substantially flow away from the medium. For example, the boron-containing binding moiety may preferentially, and reversibly, bind glycated hemoglobin, while allowing non-glycated hemoglobin, and other components of the mixture, to substantially flow away from the affinity medium. A suitable reagent (e.g., the third reagent) may then be flowed past the affinity medium to release (or liberate) the reversibly bound glycated hemoglobin, thereby allowing the glycated hemoglobin to flow substantially away from the affinity medium.

In other embodiments, the affinity medium is an immobile phase that includes a binding moiety formed via a templating agent. According to those embodiments, the affinity medium is formed in the presence of templating agent, and the templating agent is subsequently removed. Upon removal of the templating agent, the affinity medium retains a binding moiety having a shape that is substantially a mold of the shape of the templating agent. The shape of the mold may correspond to the shape of the analyte to be separated. As such, the shape-selective binding moiety may be configured to preferentially, and reversibly, bind the analyte to be separated from the mixture such that flowing a mixture including the analyte past the affinity medium results in the analyte being reversibly retained on, in, around, or adjacent to the affinity medium, while the other components of the mixture are capable of substantially flowing away from the medium. A suitable reagent (e.g., the third reagent) may then be flowed past the affinity medium to release (or liberate) the reversibly bound analyte, thereby allowing the analyte to flow substantially away from the affinity medium.

According to embodiments of the present invention the affinity medium is contained in a suitable vessel, such as a column. The column may have any suitable shape, such as a cylindrical shape, so long as the column is configured to contain the affinity medium. As set forth below, the affinity medium may be movably positioned with respect to certain other features of the cartridge or device, and thus, the column may be movably positioned as well. Alternatively, the affinity medium and/or column may have a fixed position with respect to certain other features of the device or cartridge.

Receiving Chambers

According to embodiments of the present invention, the cartridge includes at least one receiving chamber configured to receive the analyte to be separated from the mixture. The cartridge may also include at least one receiving chamber for receiving the other components of the mixture from which the analyte has been separated. According to certain exemplary embodiments, the cartridge includes a first receiving chamber configured to receive the components from which the analyte has been separated, and a second receiving chamber configured to receive the analyte (e.g., the separated analyte). For example, in certain embodiments, the first receiving chamber is configured to receive a mixture (e.g., a mixture including human or animal blood and/or at least one first reagent), from which an analyte has been separated, dispensed from a first dispensing chamber and at least one second reagent dispensed from a second dispensing chamber. Additionally, the second receiving chamber may be configured to receive the analyte (e.g., glycated hemoglobin), which has been separated from the mixture, and/or at least one third reagent. The cartridge may also include additional receiving chambers. Additionally, the materials received by the receiving chambers may be varied.

Each of the receiving chambers may receive the above-described materials by any suitable mechanism. For example, any of the receiving chambers may receive the above-described materials by harnessing the force of gravity. Alternatively, any of the receiving chambers may receive the above-described materials by harnessing a (positive or negative) pressure gradient. For example, any of the receiving chambers may receive the above-described materials by applying positive pressure, by way of a gas or liquid, to the material. Conversely, any of the receiving chambers may receive the above-described materials by applying a negative pressure, by way of a vacuum, to the materials. As another alternative, any of the receiving chambers may receive the above-described materials by harnessing a mechanical force (e.g., a force applied by a piston, plunger, or the like).

Each of the receiving chambers may include at least one aperture. For example, each receiving chamber may have a receiving aperture configured to receive the material that flows away from the affinity medium. The receiving aperture may be positioned at any suitable location in, on, or of the receiving chamber, for example, at the side of the receiving chamber adjacent to the affinity medium. The receiving aperture may include a seal to prevent the material received by the receiving from escaping the receiving chamber through the receiving aperture. In certain embodiments, each receiving chamber includes only one aperture (e.g., a receiving aperture). In certain embodiments, each receiving chamber includes one or more receiving apertures. Each receiving chamber may also include at least one additional aperture, such as, a drain aperture for draining the material received by the receiving aperture. For example, any of the receiving chambers may include a drain aperture for draining the material received by the receiving aperture for the purposes of disposing of the material or to further analyze the material, for example, by gas chromatography-mass spectrometry (GC-MS). The receiving chambers may also include venting apertures for venting the receiving chambers, as necessary.

Each receiving chamber may have any suitable shape, such as any regular or irregular three-dimensional shape. For example, each receiving chamber may have a cylindrical, cuboid (e.g., a cube or right cuboid), or any other polyhedral shape. The present invention is not particularly limited by the shapes of the receiving chambers.

Each of the receiving chambers may be formed of any suitable material. For example, any of the dispensing materials may be formed of glass, plastic or quartz. In certain embodiments, however, at least one of the materials received by the receiving chambers is measured with a spectrometer or similar instrument. According to those embodiments, at least a portion of at least one receiving chamber is compatible with a spectrometer or similar instrument. For example, any of the receiving chambers may have two opposing sides that are suitable for performing spectroscopic measurements (e.g., ultraviolet-visible spectroscopy) on a material received by the receiving chamber. That is, any of the receiving chambers may have two opposing sides that are substantially transparent to electromagnetic radiation, such as ultraviolet and/or visible light. The present invention is not particularly limited by the materials of the receiving chambers.

Exemplary Embodiment 1

Figure 2:
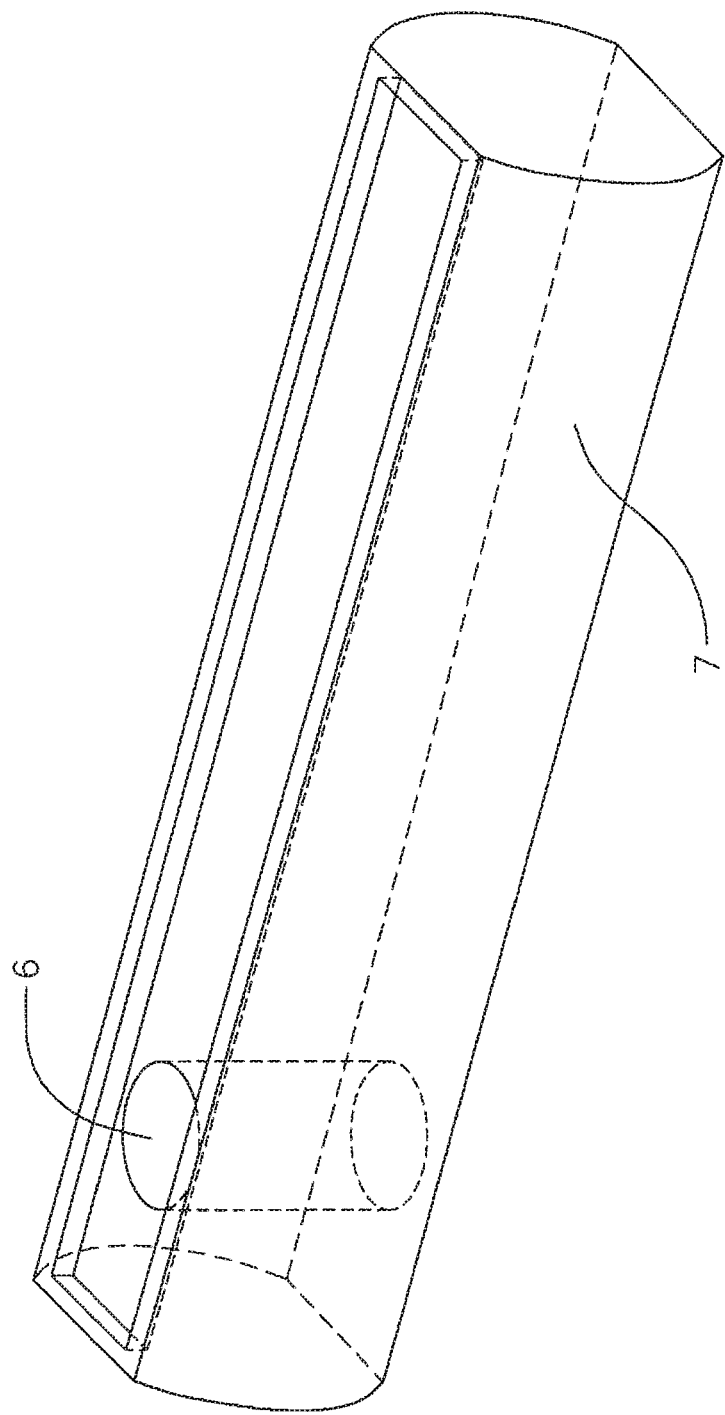
FIG. 2 is an axonometric view of a cartridge insert containing the affinity medium of exemplary embodiments of the invention.

A cartridge 10 according to one exemplary embodiment is shown in FIG. 1. As can be seen in the embodiment depicted in FIG. 1, the cartridge 10 includes a first dispensing chamber 1, a second dispensing chamber 2, a third dispensing chamber 3, a first receiving chamber 4, a second receiving chamber 5, a column 6, which includes the affinity medium, and a cartridge insert 7, which includes the column 6 containing the affinity medium. According to this embodiment, the receiving chambers 4 and 5 are adjacent to the dispensing chambers 1, 2, and 3, and the affinity medium is movably positioned between at least one dispensing chamber and at least one receiving chamber. The cartridge insert 7, which includes the column 6 containing the affinity medium, is movably positioned between the dispensing chambers and receiving chambers, and is shown separately in FIG. 2. The cartridge insert shown in FIG. 2 had the following approximate dimensions: 4.75 cm total length, 0.7419 cm interior width, and a column having a 0.6206 cm radius. The present invention, however, is not particularly limited by the dimensions of the cartridge insert. For example, according to embodiments of the present invention, the cartridge insert may have a range of suitable dimensions, such as a total length in a range of about 2.5 cm to about 7.5 cm, an interior width in a range of about 0.3 cm to about 1.5 cm, and a column having a radius in a range of about 0.3 cm to about 1.5 cm.

The cartridge 10 according to the present embodiment is shown in various stages of operation in FIGS. 3A-3C. To operate the cartridge 10 of the present embodiment, a mixture is introduced into the first dispensing chamber 1. The first dispensing chamber 1 may already include a first reagent, or the first reagent may be introduced before or after the mixture is introduced. The mixture may be introduced through the filling aperture of the first dispensing chamber 1, and the mixture may include blood. For example, the mixture may include a few microliters of human or animal blood (e.g., whole or modified blood). Once the mixture and first reagent have been introduced to the first dispensing chamber 1, the mixture and first reagent may mix so that the mixture includes the first reagent. Alternatively, the mixture and first reagent may be mixed outside of the dispensing chamber 1 so that the mixture including the first reagent may be introduced into the first dispensing chamber 1 after mixing, In certain embodiments, at least one component of the mixture and the first reagent react. For example, when the mixture includes blood, blood cells may react with the first reagent to lyse the blood cells and thereby release, among other items, hemoglobin and glycated hemoglobin. The mixture may be mixed with the first reagent for any time period suitable to complete a reaction of at least one component of the mixture and the first reagent.

When the first dispensing chamber 1 is prepared to dispense the mixture (e.g., the mixture including the first reagent), the cartridge insert 7 is moved to selectively couple the first dispensing chamber 1 to the affinity medium as shown in FIG. 3A. This movement of the cartridge insert 7 may also simultaneously, selectively couple the affinity medium to the first receiving chamber 4 as shown in FIG. 3A. Alternatively, the affinity medium may be independently, selectively coupled to the first receiving chamber 4 by an additional movement of the cartridge insert 7, which may require the presence of additional venting apertures, either in the chambers or the cartridge.

Once the first dispensing chamber 1 is selectively coupled to the affinity medium, the mixture including the first reagent is dispensed according to any of the above-described methods. The first dispensing chamber 1 may be selectively coupled to the affinity medium for any suitable period of time. For example, the first dispensing chamber 1 may be selectively coupled to the affinity medium for about 2 minutes. As the mixture is dispensed, the mixture flows toward the affinity medium. When the mixture contacts the affinity medium, the analyte is preferentially, and reversibly, bound to the affinity medium. The mixture may be held to remain in contact with the affinity medium for a suitable period of time, or the mixture may be allowed to flow past the affinity medium at its intrinsic flow rate.

When the affinity medium is selectively coupled to the first receiving chamber 4, the mixture, from which the analyte has been separated, will be allowed to flow from the affinity medium to the first receiving chamber 4. The first receiving chamber 4 then receives the mixture from which the analyte has been separated. The affinity medium may be selectively coupled to the receiving chamber 4 for any suitable period of time. For example, the first receiving chamber 4 may be selectively coupled to the affinity medium for about 2 minutes. In certain embodiments, the first dispensing chamber 1 and second receiving chamber 4 may be selectively coupled to the affinity medium for a total period of about 2 minutes.

Next, the cartridge insert 7 may be moved to selectively couple the second dispensing chamber 2 to the affinity medium as shown in FIG. 3B. This movement of the cartridge insert 7 may also simultaneously, selectively couple the affinity medium to the first receiving chamber 4 as shown in FIG. 3B. Alternatively, the affinity medium may be independently, selectively coupled to the first receiving chamber 4 by an additional movement of the cartridge insert 7, which may require the presence of additional venting apertures, either in the chambers or the cartridge.

Once the second dispensing chamber 2 is selectively coupled to the affinity medium, the second reagent is dispensed according to any of the above-described methods. The second dispensing chamber 2 may be selectively coupled to the affinity medium for any suitable period of time. For example, the second dispensing chamber 2 may be selectively coupled to the affinity medium for about 4 minutes. As the second reagent is dispensed, the second reagent flows toward the affinity medium. The second reagent then washes the affinity medium, removing materials that are not preferentially, and reversibly, bound to the affinity medium (e.g., materials other than minute quantities of the analyte). The second reagent may be held to remain in contact with the affinity medium for a suitable period of time, or the second reagent may be allowed to flow past the affinity medium at its intrinsic flow rate.

When the affinity medium is selectively coupled to the first receiving chamber 4, the second reagent will be allowed to flow from the affinity medium to the first receiving chamber 4. The first receiving chamber 4 then receives the second reagent, which may include materials washed from the affinity medium (e.g., materials other than minute quantities of the analyte). The affinity medium may be selectively coupled to the receiving chamber 4 for any suitable period of time. For example, the first receiving chamber 4 may be selectively coupled to the affinity medium for about 4 minutes. In certain embodiments, the second dispensing chamber 2 and first receiving chamber 4 may be selectively coupled to the affinity medium for a total period of about 4 minutes.

Next, the cartridge insert 7 may be moved to selectively couple the third dispensing chamber 3 to the affinity medium as shown in FIG. 3C. This movement of the cartridge insert 7 may also simultaneously, selectively couple the affinity medium to the second receiving chamber 5 as shown in FIG. 3C. Alternatively, the affinity medium may be independently, selectively coupled to the second receiving chamber 5 by an additional movement of the cartridge insert 7, which may require the presence of additional venting apertures, either in the chambers or the cartridge.

Once the third dispensing chamber 3 is selectively coupled to the affinity medium, the third reagent is dispensed according to any of the above-described methods. The third dispensing chamber 3 may be selectively coupled to the affinity medium for any suitable period of time. For example, the third dispensing chamber 3 may be selectively coupled to the affinity medium for about 2 minutes. As the third reagent is dispensed, the third reagent flows toward the affinity medium. When the third reagent contacts the affinity medium, the analyte is released (or liberated). The analyte may mix with the third reagent. The third reagent may be held to remain in contact with the affinity medium for a suitable period of time, or the third reagent may be allowed to flow past the affinity medium at its intrinsic flow rate.

When the affinity medium is selectively coupled to the second receiving chamber 5, the analyte will be allowed to flow from the affinity medium to the second receiving chamber 5. The third reagent, or a portion thereof, may also flow from the affinity medium to the second receiving chamber 5. The second receiving chamber 5 then receives the analyte, and the second receiving chamber 5 may also receive the third reagent, or a portion thereof, or a mixture of the analyte and the third reagent. The affinity medium may be selectively coupled to the second receiving chamber 5 for any suitable period of time. For example, the second receiving chamber 5 may be selectively coupled to the affinity medium for about 2 minutes. In certain embodiments, the third dispensing chamber 3 and second receiving chamber 5 may be selectively coupled to the affinity medium for a total period of about 2 minutes.

The amount of the analyte received by the second receiving chamber 5 may be spectroscopically measured (e.g., by ultraviolet-visible spectroscopy). For example, the amount of glycated hemoglobin received by the second receiving chamber 5 may be measured by ultraviolet-visible spectroscopy, for example, by measuring the optical density around the wavelength of 414 nm. The amount of certain materials received by the first receiving chamber 4 also may be spectroscopically measured (e.g., by ultraviolet-visible spectroscopy). For example, the amount of non-glycated hemoglobin received by the first receiving chamber 4 may be measured by ultraviolet-visible (UV-Vis) spectroscopy. Alternatively, the materials of the receiving chambers may be discharged to another vessel before being spectroscopically measured.

By comparing the amounts of the materials received by the first receiving chamber 4 and the second receiving chamber 5, the amount of the analyte, as compared to another component of the original mixture, can be determined. For example, by comparing the amount of non-glycated hemoglobin received by the first receiving chamber 4 to the amount of glycated hemoglobin received in the second receiving chamber 5, the relative amount of glycated hemoglobin, as compared to the amount of non-glycated hemoglobin in the original blood, can be determined. Thus, according to this embodiment, the level of glycated hemoglobin in a patient's blood can be determined.

According to certain embodiments, the materials received in the receiving chambers may then be discharged for either disposal, further analysis, or both. For example, certain materials received in the receiving chambers may be discharged for further spectroscopic analysis. In certain embodiments, certain materials received in the receiving chambers may be discharged for gas chromatography-mass spectrometry (GCMS) analysis.

Exemplary Embodiment 2

Figure 4:
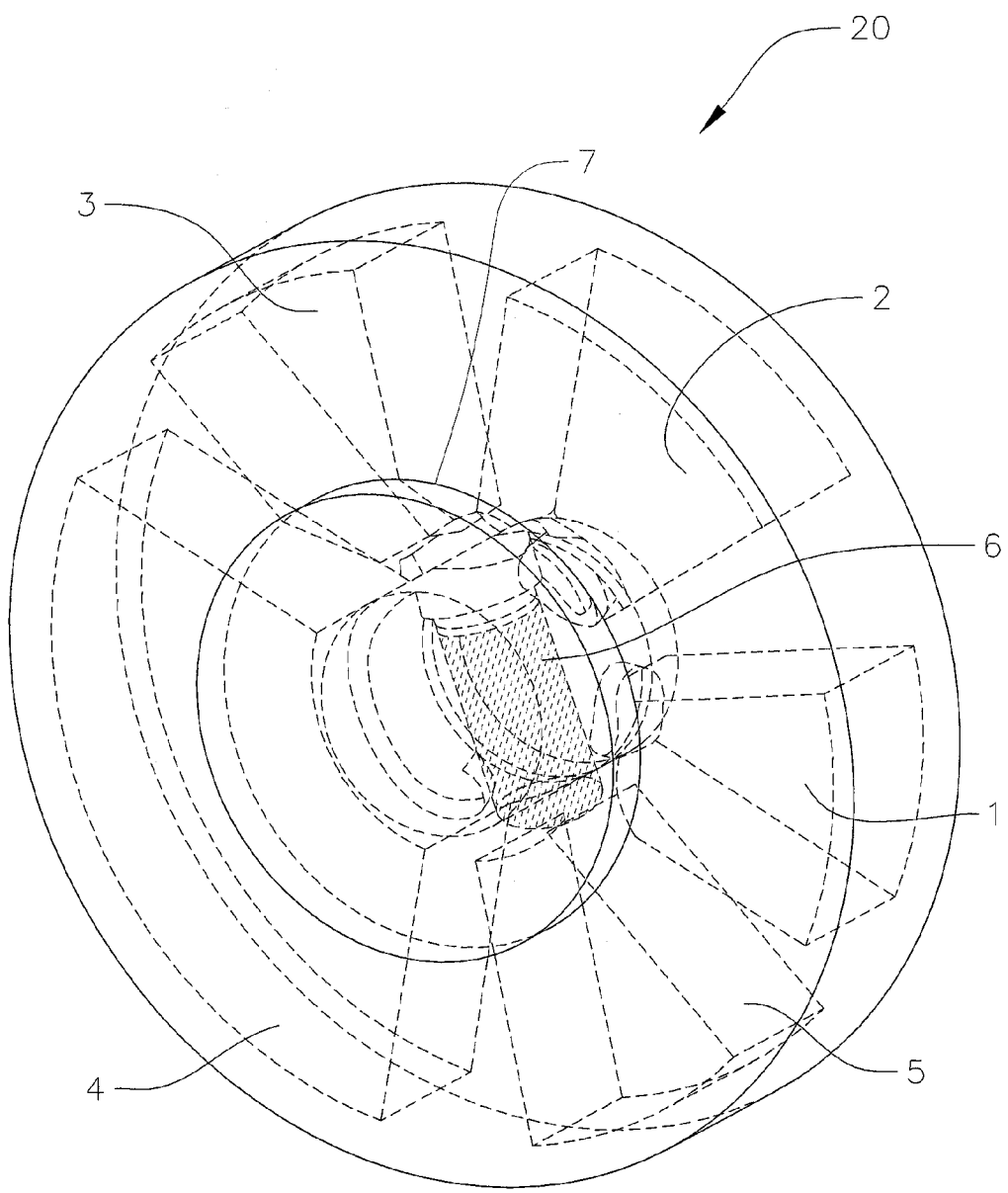
FIG. 4 is an axonometric view of a cartridge according to alternative exemplary embodiments of the present invention.
Figure 5:
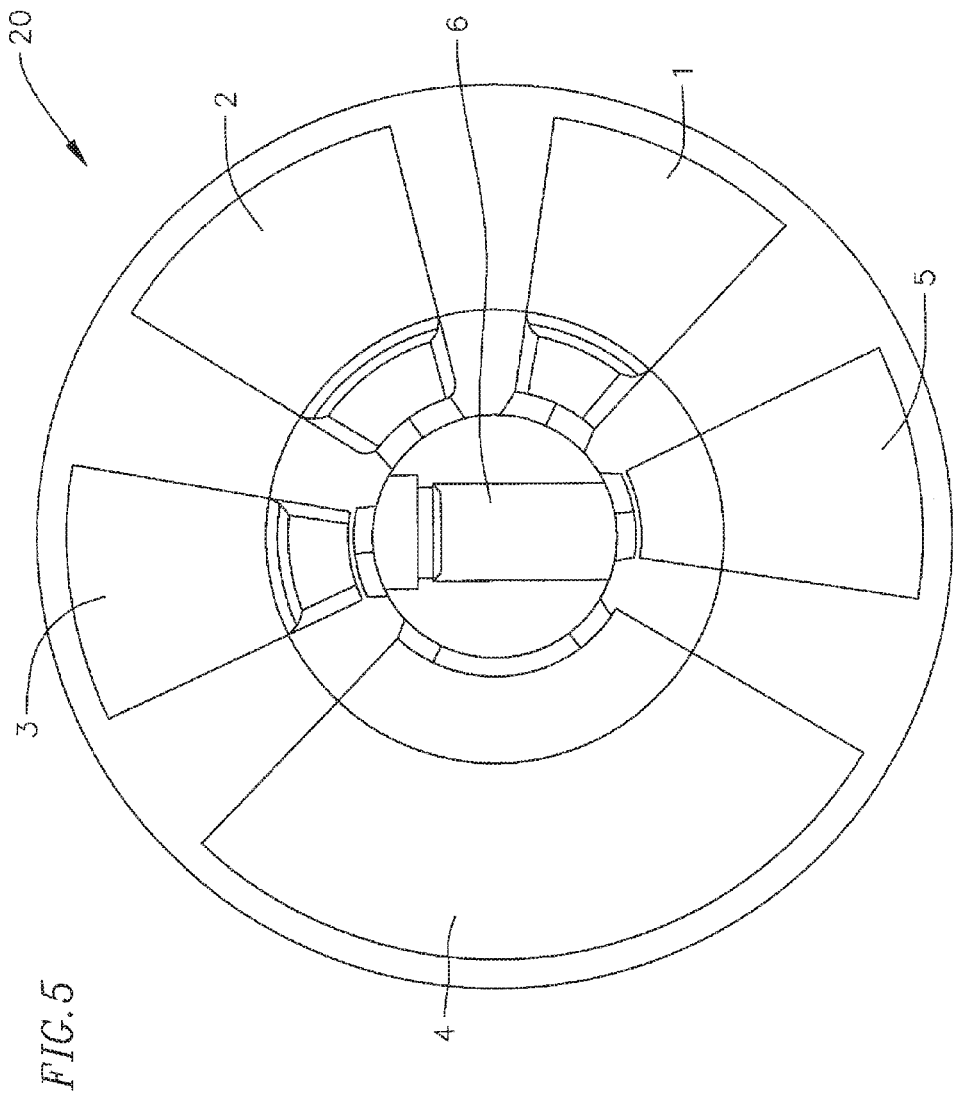
FIG. 5 is another view of the cartridge according to the exemplary embodiment shown in FIG. 4.

A cartridge 20 according to another exemplary embodiment is shown in FIG. 4. An additional view of the cartridge 20 according to this exemplary embodiment is shown in FIG. 5. As can be seen in the embodiment depicted in FIGS. 4 and 5, the cartridge 20 includes a first dispensing chamber 1, a second dispensing chamber 2, a third dispensing chamber 3, a first receiving chamber 4, a second receiving chamber 5, an insert 7 and a column 6, which includes the affinity medium. According to this embodiment, the receiving chambers 4 and 5 are movably positioned adjacent to the affinity medium. Additionally, the dispensing chambers 1, 2, and 3 are movably positioned adjacent to the affinity medium. According to the present embodiment, the cartridge is configured to selectively couple each of the dispensing chambers to the affinity medium according to the position of each of the dispensing chambers. Additionally, in this embodiment, the cartridge is configured to selectively couple the affinity medium to each of the receiving chambers according to the position of each of the receiving chambers. Certain aspects of the operation of this embodiment are similar to those described above, and the description of such aspects will not be repeated.

When the first dispensing chamber 1 is prepared to dispense the mixture (e.g., the mixture including the first reagent), one or more of the dispensing chambers is moved (e.g., rotated) to selectively couple the first dispensing chamber 1 to the affinity medium. Additionally, one or more of the receiving chambers may be simultaneously moved (e.g., rotated) to simultaneously selectively couple the affinity medium to the first receiving chamber 4. Alternatively, the affinity medium may be independently, selectively coupled to the first receiving chamber 4 by an independent movement (e.g., rotation) of one or more of the receiving chambers, which may require the presence of additional venting apertures, either in the chambers or the cartridge.

Once the first dispensing chamber 1 is selectively coupled to the affinity medium, the mixture including the first reagent is dispensed according to any of the above-described methods. The first dispensing chamber 1 may be selectively coupled to the affinity medium for any suitable period of time. For example, the first dispensing chamber 1 may be selectively coupled to the affinity medium for about 2 minutes. As the mixture is dispensed, the mixture flows toward the affinity medium. When the mixture contacts the affinity medium, the analyte is preferentially, and reversibly, bound to the affinity medium. The mixture may be held to remain in contact with the affinity medium for a suitable period of time, or the mixture may be allowed to flow past the affinity medium at its intrinsic flow rate.

When the affinity medium is selectively coupled to the first receiving chamber 4, the mixture, from which the analyte has been separated, will be allowed to flow from the affinity medium to the first receiving chamber 4. The first receiving chamber 4 then receives the mixture from which the analyte has been separated. The affinity medium may be selectively coupled to the receiving chamber 4 for any suitable period of time. For example, the first receiving chamber 4 may be selectively coupled to the affinity medium for about 2 minutes. In certain embodiments, the first dispensing chamber 1 and second receiving chamber 4 may be selectively coupled to the affinity medium for a total period of about 2 minutes.

Next, one or more of the dispensing chambers may be moved (e.g., rotated) to selectively couple the second dispensing chamber 2 to the affinity medium. Additionally, one or more of the receiving chambers may be simultaneously moved (e.g., rotated) to simultaneously selectively couple the affinity medium to the first receiving chamber 4. Alternatively, the affinity medium may be independently, selectively coupled to the first receiving chamber 4 by an independent movement (e.g., rotation) of one or more of the receiving chambers, which may require the presence of additional venting apertures, either in the chambers or the cartridge.

Once the second dispensing chamber 2 is selectively coupled to the affinity medium, the second reagent is dispensed according to any of the above-described methods. The second dispensing chamber 2 may be selectively coupled to the affinity medium for any suitable period of time. For example, the second dispensing chamber 2 may be selectively coupled to the affinity medium for about 4 minutes. As the second reagent is dispensed, the second reagent flows toward the affinity medium. The second reagent then washes the affinity medium, removing materials that are not preferentially, and reversibly, bound to the affinity medium (e.g., materials other than minute quantities of the analyte). The second reagent may be held to remain in contact with the affinity medium for a suitable period of time, or the second reagent may be allowed to flow past the affinity medium at its intrinsic flow rate.

When the affinity medium is selectively coupled to the first receiving chamber 4, the second reagent will be allowed to flow from the affinity medium to the first receiving chamber 4. The first receiving chamber 4 then receives the second reagent, which may include materials washed from the affinity medium (e.g., materials other than minute quantities of the analyte). The affinity medium may be selectively coupled to the receiving chamber 4 for any suitable period of time. For example, the first receiving chamber 4 may be selectively coupled to the affinity medium for about 4 minutes. In certain embodiments, the second dispensing chamber 2 and first receiving chamber 4 may be selectively coupled to the affinity medium for a total period of about 4 minutes.

Next, one or more of the dispensing chambers may be moved (e.g., rotated) to selectively couple the third dispensing chamber 3 to the affinity medium. Additionally, one or more of the receiving chambers may be simultaneously moved (e.g., rotated) to simultaneously selectively couple the affinity medium to the second receiving chamber 5. Alternatively, the affinity medium may be independently, selectively coupled to the second receiving chamber 5 by an independent movement (e.g., rotation) of one or more of the receiving chambers, which may require the presence of additional venting apertures, either in the chambers or the cartridge.

Once the third dispensing chamber 3 is selectively coupled to the affinity medium, the third reagent is dispensed according to any of the above-described methods. The third dispensing chamber 3 may be selectively coupled to the affinity medium for any suitable period of time. For example, the third dispensing chamber 3 may be selectively coupled to the affinity medium for about 2 minutes. As the third reagent is dispensed, the third reagent flows toward the affinity medium. When the third reagent contacts the affinity medium, the analyte is released (or liberated). The analyte may mix with the third reagent. The third reagent may be held to remain in contact with the affinity medium for a suitable period of time, or the third reagent may be allowed to flow past the affinity medium at its intrinsic flow rate.

When the affinity medium is selectively coupled to the second receiving chamber 5, the analyte will be allowed to flow from the affinity medium to the second receiving chamber 5. The third reagent, or a portion thereof, may also flow from the affinity medium to the second receiving chamber 5. The second receiving chamber 5 then receives the analyte, and the second receiving chamber 5 may also receive the third reagent, or a portion thereof, or a mixture of the analyte and the third reagent. The affinity medium may be selectively coupled to the second receiving chamber 5 for any suitable period of time. For example, the second receiving chamber 5 may be selectively coupled to the affinity medium for about 2 minutes. In certain embodiments, the third dispensing chamber 3 and second receiving chamber 5 may be selectively coupled to the affinity medium for a total period of about 2 minutes.

The amount of the analyte received by the second receiving chamber 5 may be spectroscopically measured (e.g., by ultraviolet-visible spectroscopy). For example, the amount of glycated hemoglobin received by the second receiving chamber 5 may be measured by ultraviolet-visible spectroscopy, for example, by measuring the optical density around the wavelength of 414 nm. The amount of certain materials received by the first receiving chamber 4 also may be spectroscopically measured (e.g., by ultraviolet-visible spectroscopy). For example, the amount of non-glycated hemoglobin received by the first receiving chamber 4 may be measured by ultraviolet-visible (UV-Vis) spectroscopy. Alternatively, the materials of the receiving chambers may be discharged to another vessel before being spectroscopically measured.

By comparing the amounts of the materials received by the first receiving chamber 4 and the second receiving chamber 5, the amount of the analyte, as compared to another component of the original mixture, can be determined. For example, by comparing the amount of non-glycated hemoglobin received by the first receiving chamber 4 to the amount of glycated hemoglobin received in the second receiving chamber 5, the relative amount of glycated hemoglobin, as compared to the amount of non-glycated hemoglobin in the original blood, can be determined. Thus, according to this embodiment, the level of glycated hemoglobin in a patient's blood can be determined.

According to certain embodiments, the materials received in the receiving chambers may then be discharged for either disposal, further analysis, or both. For example, certain materials received in the receiving chambers may be discharged for further spectroscopic analysis. In certain embodiments, certain materials received in the receiving chambers may be discharged for gas chromatography-mass spectrometry (GCMS) analysis.

Exemplary Embodiment 3

Figure 6:
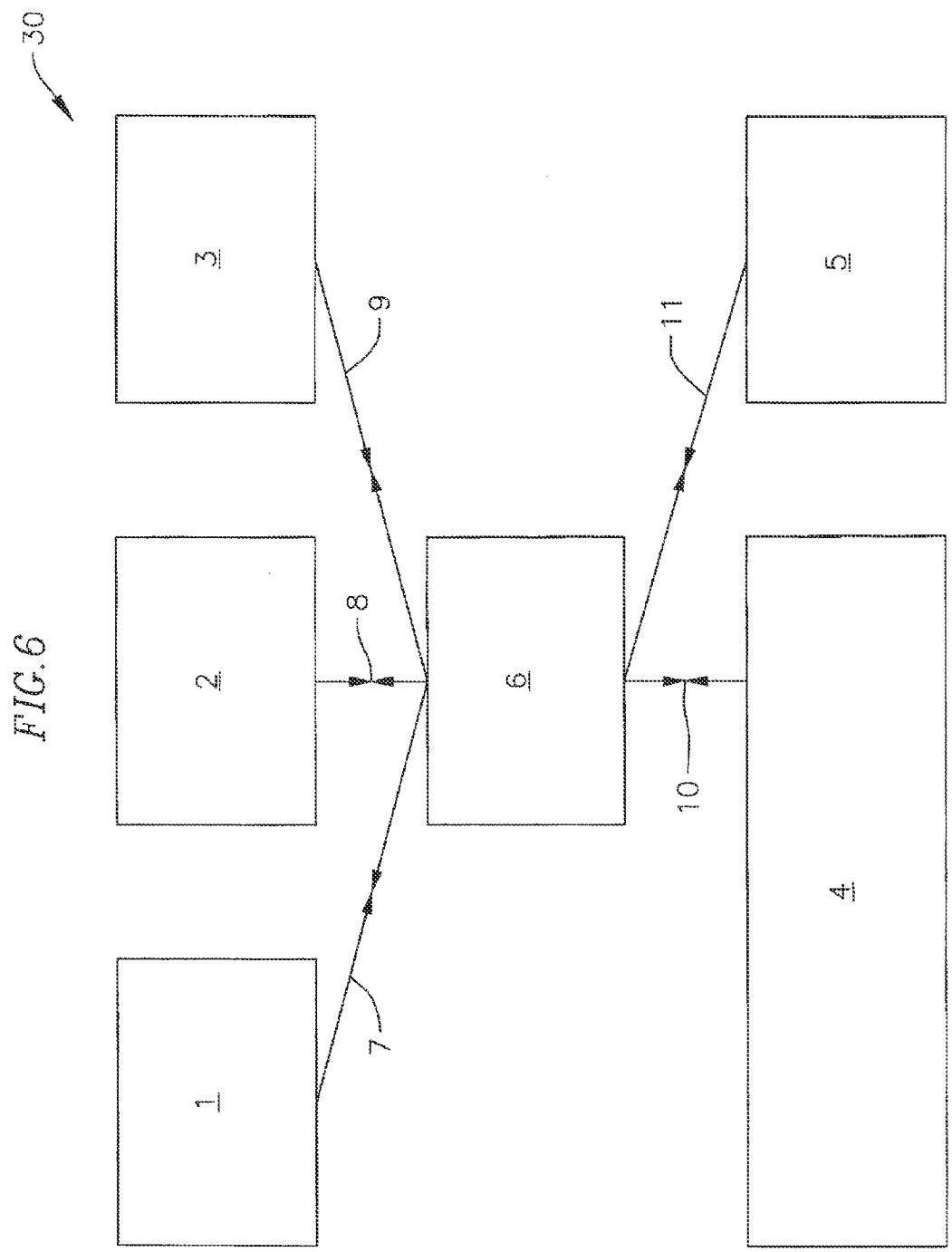
FIG. 6 is a schematic view of a cartridge according to another alternative exemplary embodiment of the present invention.

A cartridge 30 according to another exemplary embodiment is shown in FIG. 6. As can be seen in the embodiment depicted in FIG. 6, the cartridge 30 includes a first dispensing chamber 1, a second dispensing chamber 2, a third dispensing chamber 3, a first receiving chamber 4, a second receiving chamber 5, and a column 6, which includes the affinity medium. The cartridge of this embodiment also includes a first dispensing flow path 7, a second dispensing flow path 8, a third dispensing flow path 9, a first receiving flow path 10, and a second receiving flow path 11, each of which may include a valve or similar device for engaging the flow path. According to embodiments of the present invention, a flow path may be an opening or an aperture having a width greater than its length, or it may be a conduit or channel having a length greater than its width.

According to the present embodiment, the cartridge is configured to selectively couple each of the dispensing chambers to the affinity medium by way of the corresponding dispensing flow path, which is engaged by operating a valve or similar device. Additionally, in this embodiment, the cartridge is configured to selectively couple the affinity medium to each of the receiving chambers by way of the corresponding receiving flow path, which is engaged by operating a valve or similar device. Certain aspects of the operation of this embodiment are similar to those described above, and the description of such aspects will not be repeated, When the first dispensing chamber 1 is prepared to dispense the mixture (e.g., the mixture including the first reagent), the first dispensing flow path is engaged (e.g., by operating a valve or similar device) to selectively couple the first dispensing chamber 1 to the affinity medium. Additionally, the affinity medium may be selectively coupled to the first receiving chamber 4, by simultaneously engaging the first receiving flow path. Alternatively, the affinity medium may be selectively coupled to the first receiving chamber 4 by independently engaging the first receiving flow path, which may require the presence of additional venting apertures, either in the chambers or the cartridge.

Once the first dispensing chamber 1 is selectively coupled to the affinity medium, the mixture including the first reagent is dispensed according to any of the above-described methods. The first dispensing chamber 1 may be selectively coupled to the affinity medium for any suitable period of time. For example, the first dispensing chamber 1 may be selectively coupled to the affinity medium for about 2 minutes. As the mixture is dispensed, the mixture flows toward the affinity medium. When the mixture contacts the affinity medium, the analyte is preferentially, and reversibly, bound to the affinity medium. The mixture may be held to remain in contact with the affinity medium for a suitable period of time, or the mixture may be allowed to flow past the affinity medium at its intrinsic flow rate.

When the affinity medium is selectively coupled to the first receiving chamber 4, the mixture, from which the analyte has been separated, will be allowed to flow from the affinity medium to the first receiving chamber 4. The first receiving chamber 4 then receives the mixture from which the analyte has been separated. The affinity medium may be selectively coupled to the receiving chamber 4 for any suitable period of time. For example, the first receiving chamber 4 may be selectively coupled to the affinity medium for about 2 minutes. In certain embodiments, the first dispensing chamber 1 and second receiving chamber 4 may be selectively coupled to the affinity medium for a total period of about 2 minutes.

Next, the second dispensing flow path is engaged to selectively couple the second dispensing chamber 2 is selectively coupled to the affinity medium. Additionally, the affinity medium may be selectively coupled to the first receiving chamber 4, by simultaneously engaging the first receiving flow path. Alternatively, the affinity medium may be selectively coupled to the first receiving chamber 4 by independently engaging the first receiving flow path, which may require the presence of additional venting apertures, either in the chambers or the cartridge.

Once the second dispensing chamber 2 is selectively coupled to the affinity medium, the second reagent is dispensed according to any of the above-described methods. The second dispensing chamber 2 may be selectively coupled to the affinity medium for any suitable period of time. For example, the second dispensing chamber 2 may be selectively coupled to the affinity medium for about 4 minutes. As the second reagent is dispensed, the second reagent flows toward the affinity medium. The second reagent then washes the affinity medium, removing materials that are not preferentially, and reversibly, bound to the affinity medium (e.g., materials other than minute quantities of the analyte). The second reagent may be held to remain in contact with the affinity medium for a suitable period of time, or the second reagent may be allowed to flow past the affinity medium at its intrinsic flow rate.

When the affinity medium is selectively coupled to the first receiving chamber 4, the second reagent will be allowed to flow from the affinity medium to the first receiving chamber 4. The first receiving chamber 4 then receives the second reagent, which may include materials washed from the affinity medium (e.g., materials other than minute quantities of the analyte). The affinity medium may be selectively coupled to the receiving chamber 4 for any suitable period of time. For example, the first receiving chamber 4 may be selectively coupled to the affinity medium for about 4 minutes. In certain embodiments, the second dispensing chamber 2 and first receiving chamber 4 may be selectively coupled to the affinity medium for a total period of about 4 minutes.

Next, the third dispensing flow path is engaged to selectively couple the third dispensing chamber 3 to the affinity medium. Additionally, the affinity medium may be selectively coupled to the second receiving chamber 5, by simultaneously engaging the second receiving flow path. Alternatively, the affinity medium may be selectively coupled to the second receiving chamber 5 by independently engaging the second receiving flow path, which may require the presence of additional venting apertures, either in the chambers or the cartridge.

Once the third dispensing chamber 3 is selectively coupled to the affinity medium, the third reagent is dispensed according to any of the above-described methods. The third dispensing chamber 3 may be selectively coupled to the affinity medium for any suitable period of time. For example, the third dispensing chamber 3 may be selectively coupled to the affinity medium for about 2 minutes. As the third reagent is dispensed, the third reagent flows toward the affinity medium. When the third reagent contacts the affinity medium, the analyte is released (or liberated). The analyte may mix with the third reagent. The third reagent may be held to remain in contact with the affinity medium for a suitable period of time, or the third reagent may be allowed to flow past the affinity medium at its intrinsic flow rate.

When the affinity medium is selectively coupled to the second receiving chamber 5, the analyte will be allowed to flow from the affinity medium to the second receiving chamber 5. The third reagent, or a portion thereof, may also flow from the affinity medium to the second receiving chamber 5. The second receiving chamber 5 then receives the analyte, and the second receiving chamber 5 may also receive the third reagent, or a portion thereof, or a mixture of the analyte and the third reagent. The affinity medium may be selectively coupled to the second receiving chamber 5 for any suitable period of time. For example, the second receiving chamber 5 may be selectively coupled to the affinity medium for about 2 minutes. In certain embodiments, the third dispensing chamber 3 and second receiving chamber 5 may be selectively coupled to the affinity medium for a total period of about 2 minutes.

The amount of the analyte received by the second receiving chamber 5 may be spectroscopically measured (e.g., by ultraviolet-visible spectroscopy). For example, the amount of glycated hemoglobin received by the second receiving chamber 5 may be measured by ultraviolet-visible spectroscopy, for example, by measuring the optical density around the wavelength of 414 nm. The amount of certain materials received by the first receiving chamber 4 also may be spectroscopically measured (e.g., by ultraviolet-visible spectroscopy). For example, the amount of non-glycated hemoglobin received by the first receiving chamber 4 may be measured by ultraviolet-visible (UV-Vis) spectroscopy. Alternatively, the materials of the receiving chambers may be discharged to another vessel before being spectroscopically measured.

By comparing the amounts of the materials received by the first receiving chamber 4 and the second receiving chamber 5, the amount of the analyte, as compared to another component of the original mixture, can be determined. For example, by comparing the amount of non-glycated hemoglobin received by the first receiving chamber 4 to the amount of glycated hemoglobin received in the second receiving chamber 5, the relative amount of glycated hemoglobin, as compared to the amount of non-glycated hemoglobin in the original blood, can be determined. Thus, according to this embodiment, the level of glycated hemoglobin in a patient's blood can be determined.

According to certain embodiments, the materials received in the receiving chambers may then be discharged for either disposal, further analysis, or both. For example, certain materials received in the receiving chambers may be discharged for further spectroscopic analysis. In certain embodiments, certain materials received in the receiving chambers may be discharged for gas chromatography-mass spectrometry (GCMS) analysis.

Exemplary Embodiment 4

Figure 7:
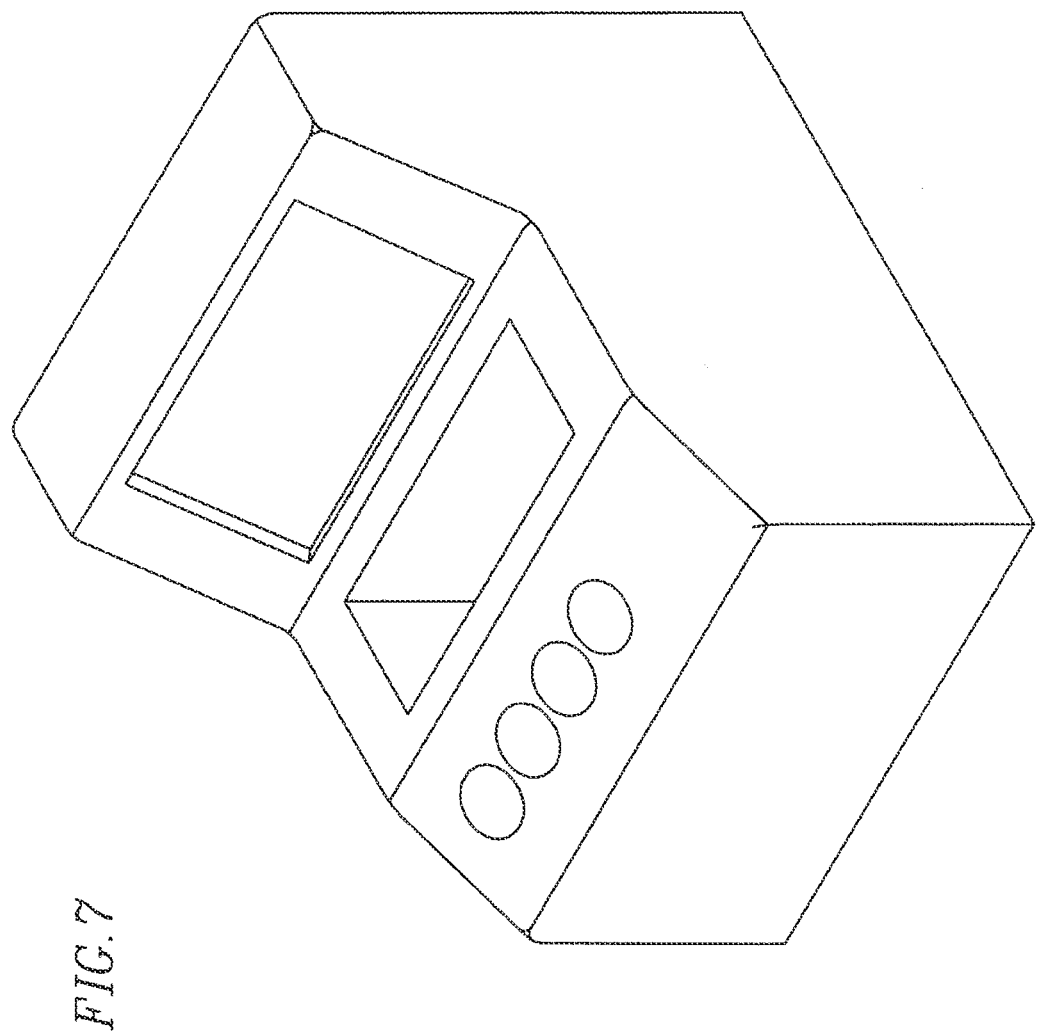
FIG. 7 is an axonometric view of a system for measuring an amount of an analyte according to exemplary embodiments of the present invention.

A system according to embodiments of the present invention is shown in FIG. 7. The system can be configured to be compatible with a cartridge according to any of the embodiments of the present invention. As can be seen in FIG. 7, the system includes a cartridge compartment adapted to work with the cartridge. The system may also include a keypad so that a user can interact with the system, and the system may include an LCD display for displaying information to the user, such as the results of a spectroscopic measurement. In certain embodiments, the system also includes a spectrometer for measuring an amount of an analyte. For example, the system may include a light source and a detector for acquiring spectroscopic signals. The system may also include one or more processors for processing the spectroscopic signals.

Additionally, the system may also include mechanisms for operating the various features of the cartridge. For example, the system may include a piston, mechanical arm, or rotating mechanism for moving components of the cartridge, such as the dispensing chambers, receiving chambers, and/or affinity medium. The system may also include mechanisms (e.g., valves) for selectively coupling the various features of the cartridge (e.g., the chambers to the affinity medium, and vice versa), and the system may include pneumatic tubes or valves that cause materials to move through the cartridge.

According to certain embodiments, the steps performed by the system are automated. For example, the user may be able to operate the system by pressing a single button, resulting in each step being carried out automatically. Alternatively, the user may be able to selectively activate various steps of the system according to the user's input.

The following examples are presented for illustrative purposes only and are not be viewed as limiting the scope of the present invention. Unless otherwise indicated, all parts and percentages in the following examples, as well as throughout the specification, are by weight.

Methods

Figure 8:
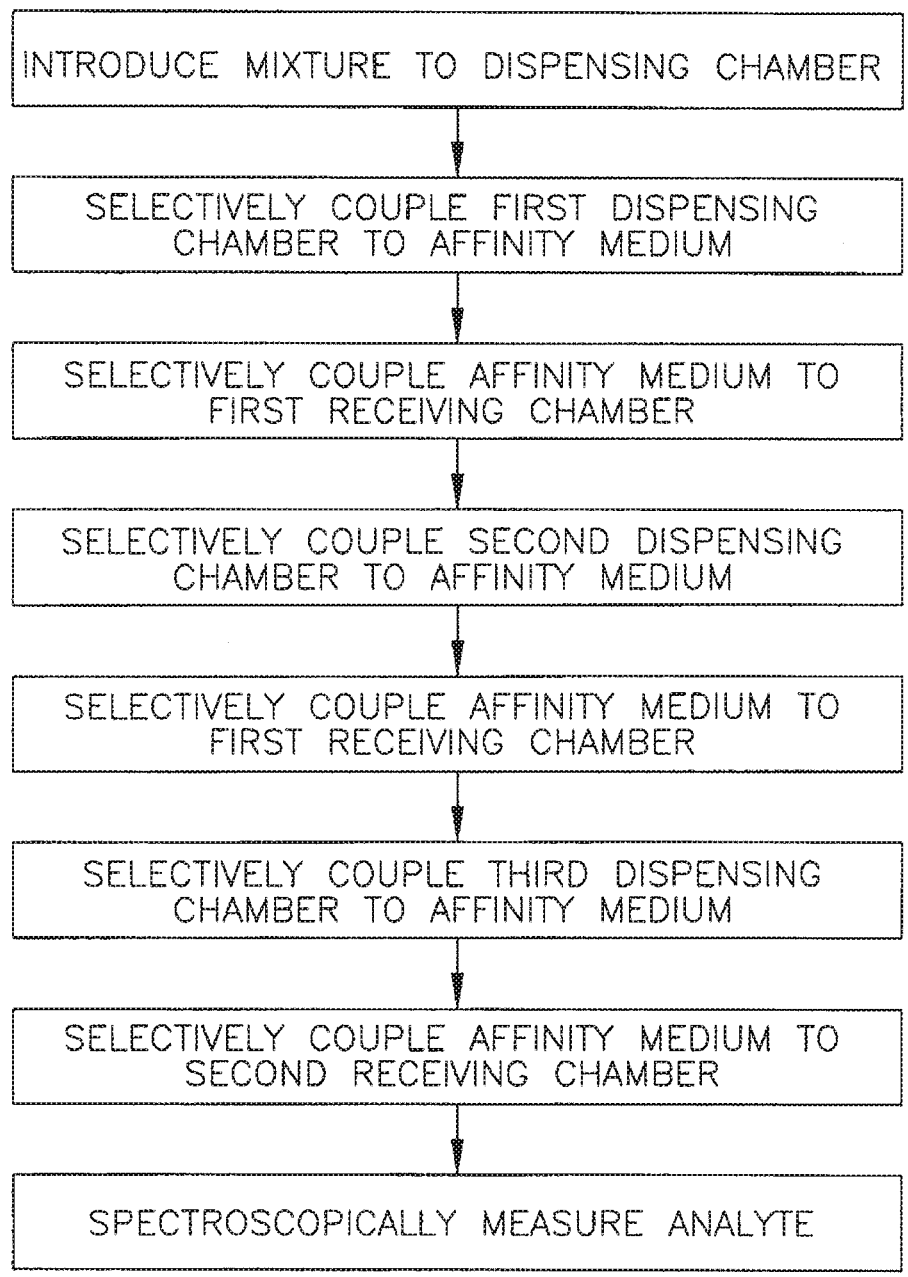
FIG. 8 is a block diagram that exemplifies a general process by which an analyte can be separated from a mixture and the amount of the analyte can be measured.

Embodiments of the present invention are also directed to methods of measuring the amount of an analyte. For example, a method according to an exemplary embodiment includes: separating the analyte from a mixture using an affinity medium and spectroscopically measuring the amount of the analyte. In certain embodiments the method of measuring the amount of an analyte includes: selectively coupling a first dispensing chamber to an affinity medium to allow a first reagent and a mixture including the analyte to flow past the affinity medium, thereby binding the analyte to the affinity medium; selectively coupling the affinity medium to a first receiving chamber to allow the residual first reagent and mixture to flow into the first receiving chamber; selectively coupling a second dispensing chamber to the affinity medium to allow a second reagent to flow past the affinity medium and bound analyte, thereby washing the affinity medium and bound analyte; selectively coupling the affinity medium to the first receiving chamber to allow the residual second reagent to flow into the first receiving chamber; selectively coupling a third dispensing chamber to the affinity medium to allow a third reagent to flow past the affinity medium, thereby releasing the bound analyte; selectively coupling the affinity medium to a second receiving chamber to allow the residual third reagent and analyte to flow into the second receiving chamber; and spectroscopically measuring the amount of the analyte, wherein the first, second, and third reagents are the same or different. FIG. 8 is a block diagram that depicts exemplary embodiments of the present invention in which an analyte can be separated from a mixture and the amount of the analyte can be measured. In certain embodiments, the method of measuring the amount of the analyte includes separating glycated hemoglobin from non-glycated hemoglobin, spectroscopically measuring the amount of glycated hemoglobin, and spectroscopically measuring the amount of non-glycated hemoglobin.

Example 1

An exemplary affinity medium was prepared as follows. Wet agarose (10 g or about 20 L) was washed with 300 mL of $H_2O$ and then suspended in 10 mL of 0.5 M sodium phosphate buffer. Sodium borohydride (100 mg) was immediately added to the gel with stirring. Crosslinker (e.g., divinyl sulfone) was added to the beaker and was stirred at room temperature for 16 hours. After stirring, the agarose gel was washed with water 5 times by centrifugation at 4000 rpm for 10 minutes each. The gel was then washed with 200 mL of $H_2O$ using filtration and was suspended in 10 mL of 1M NaOH.

Next, m-aminophenylboronic acid (mAPBA) was coupled to the cross-linked agarose gel as follows. The cross-linked agarose gel was washed thoroughly with 500 mL of water using filtration, and then suspended in 10 mL of 2.5 M NaOH. 15 mg of sodium borohydride was immediately added followed by 2.0 mL of the spacer (e.g., any oxirane-containing organohalide with 3-10 carbon atoms). The mixture was stirred at room temperature for 18 hours. The gel was then washed excessively and immediately coupled with mAPBA (3-aminophenylboronic acid).

The gel was suspended in 10 mL of 1 M sodium carbonate (pH ~10). 600 mg of mAPBA (3-aminophenylboronic acid hemisulfate salt) was added to the gel. The mixture was stirred at room temperature for 72 hours. After that, the gel was heated to ~55° C. for 20 minutes. After deactivation, the gel was washed with: 50 mL of 0.1 M sodium bicarbonate (pH ~8.5), 100 mL of water, 50 mL 95% ethanol, 100 mL of water, 50 mL Of 10% (v/v) acetic acid, and 100 mL of water.

A first reagent was prepared from a mixture of 10-50 mM 4-(2-hydroxyethyl)-1-piperazineethanesulfonic acid (HEPES), 20-50 mM magnesium chloride, 1.0 g sodium azide, and 1.0 L of water.

A second reagent was prepared from a mixture of 10-50 mM 4-(2-hydroxyethyl)-1-piperazineethanesulfonic acid (HEPES), 20-50 mM magnesium chloride, 1.0 g sodium azide, Triton™ X-100 (0.1-1%), and 1.0 L of water.

A third reagent was prepared from a mixture of 50-100 mM (or 18.22 g) sorbitol, 50-100 mM Tris (12.11 g), 0.5-1.5 g sodium azide, 0.2-0.8% Triton™-X-100, and 1.0 L of water.

The above-described affinity medium, first, second and third reagents were then used to separate glycated hemoglobin from a sample of human blood. The blood was mixed with the second reagent and then exposed to the affinity medium. The affinity medium was then washed with the first reagent. After the first reagent emerged from the affinity medium as a colorless fraction, the glycated hemoglobin was eluted with the third reagent. The amount of glycated hemoglobin that eluted from the affinity medium was then measured spectroscopically.

Example 2

A system was prepared according to the first exemplary embodiment. The cartridge had the following dimensions: 4.2 cm total height, 4.0 cm total width, 1.5 cm total depth, and filling apertures of 0.3 cm. The present invention, however, is not particularly limited by the dimensions of the cartridge. For example, according to embodiments of the present invention, the cartridge may have a range of suitable dimensions, such as a total height in a range of about 2 cm to about 6 cm, a total width in a range of about 2 cm to about 6 cm, a total depth in a range of about 0.5 cm to about 3 cm, and apertures of about 0.1 cm to about 0.6 cm.

The effectiveness of embodiments of the present invention was evaluated for both animal and human blood. The measurements were taken using the above-described affinity medium and reagents. According to an embodiment of the present invention, it was determined that a sample of commercial human whole blood contained 5.78% GHb A1c; while horse blood contained 2.56% GHb A1c. Both values are consistent with literature data. See e.g., Sacks, D. B.; Bruns, D. E.; Goldstein, D. E.; Maclaren, N. K.; McDonald, J. M.; Parrott, M. Guidelines and recommendations for laboratory analysis in the diagnosis and management of diabetes mellitus. *Clinical Chemistry*, 48(3), 436-72 (2002); and Shahbazkia, H.; Nazifi, S. Determination of glycated haemoglobin in horses by cation exchange chromatography, *Comparative Clinical Pathology*, 14(3), 168-170 (2005). Additionally, the GHb A1c concentration was measured for five commercial GHB A1c standards. FIG. 9 shows the correlation between the reported GHB A1c concentration for each of the five commercial GHb A1c standards and the measured values. The reported GHB A1c concentration of the standard is shown to the left, and the GHB A1c concentration of the standard as measured by an embodiment of the present invention is shown to the right. As can be seen from FIG. 9, each of the five standard samples shows a strong correlation between the reported concentration of GHb A1c and the concentration of GHB A1c as measured according to an embodiment of the present invention.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof. Also, in the context of the present application, when a first element is referred to as being "adjacent to" or "movably adjacent to" another element(s), it can be directly or indirectly on, over, under, below, or next to the other element(s). Thus, in some embodiments, two adjacent features are literally right next to each other, while in other embodiments, the same two features are separated by one or more additional feature(s). In each case, one of the two features is "adjacent to" or "movably adjacent to" the other feature.

Similarly, in the preceding description and in the claims, various features may be described as being "positioned over," "disposed over," "located on," or "on" one or more additional features. This language simply denotes the relative positions of the features. In each case, one of the two features is considered to be "positioned over," "disposed over," "located on," or "on" the other layer. Also, "over" or "on" can mean "below." For example, a feature that is "over" or "on" another feature can also be considered "below" the other feature, depending upon the point of view.

Additionally, in the preceding description and in the claims, various features may be described as being "between" other features. This language simply denotes the relative positions of the features. Thus, in some embodiments, one feature is directly between at least two other features, while in other embodiments, the feature is indirectly between at least two other features. In addition, in some embodiments, there may be other features between the feature and the at least two other features, while in other embodiments, the feature is literally right next to at least one of the at least two other features.

Furthermore, in the preceding description, and in the claims, various features are described as being "configured to selectively couple" one feature to another feature. This language simply denotes that a feature may be selectively coupled to another feature to allow a rial to be communicated, directly or indirectly, from the first feature to the second feature. The features may be selectively coupled to one another independently of the coupling of other features. Alternatively, certain features may be coupled to one another simultaneously with the coupling of other features to one another.

What is claimed is:

1. A cartridge for separating an analyte from a mixture, the cartridge comprising:
    two or more dispensing chambers at a top of the cartridge, each dispensing chamber having a dispensing aperture;
    two or more receiving chambers at a bottom of the cartridge, each receiving chamber having a receiving aperture, the receiving chambers being positioned relative to the dispensing chambers so that the receiving chambers are capable of receiving the mixture from the dispensing chambers; and
    an insert comprising a column comprising an affinity medium, the insert being configured to be positioned between at least one of the dispensing chambers and at least one of the receiving chambers to form a bottom of at least one of the dispensing apertures to block the at least one dispensing aperture,
    wherein at least one of the dispensing chambers, the receiving chambers, or the insert is configured to move relative to the others to position the column comprising the affinity medium to be adjacent to one of the dispensing chambers to open the at least one dispensing aperture to form at least one dispensing flow path between the dispensing chamber and the affinity medium, and
    wherein at least one of the dispensing chambers, the receiving chambers, or the insert is configured to move relative to the others to position the column comprising the affinity medium to be adjacent to one of the receiving chambers to open the at least one receiving aperture to form at least one receiving flow path between the affinity medium and the receiving chamber.

2. The cartridge of claim 1, wherein the insert is movably positioned between at least one of the dispensing chambers and at least one of the receiving chambers.

3. The cartridge of claim 2, wherein the cartridge is configured to selectively couple each of the dispensing chambers to the affinity medium according to the position of the insert.

4. The cartridge of claim 2, wherein the cartridge is configured to selectively couple the affinity medium to each of the receiving chambers according to the position of the insert.

5. The cartridge of claim 1, wherein the dispensing chambers and receiving chambers are movably positioned adjacent to the insert.

6. The cartridge of claim 5, wherein:
    the cartridge is configured to selectively couple each of the dispensing chambers to the affinity medium according to the position of each of the dispensing chambers, and
    the cartridge is configured to selectively couple the affinity medium to each of the receiving chambers according to the position of each of the receiving chambers.

7. The cartridge of claim 1, wherein:
the at least one dispensing flow path is configured to selectively couple one of the dispensing chambers to the affinity medium, and
the at least one receiving flow path is configured to selectively couple the affinity medium to one of the receiving chambers.

8. The cartridge of claim 1, wherein at least one of the dispensing chambers is configured to dispense a mixture comprising at least one reagent.

9. The cartridge of claim 1, wherein the at least one reagent is configured to lyse human blood cells.

10. The cartridge of claim 1, wherein at least one of the receiving chambers is configured to receive the analyte.

11. The cartridge of claim 1, wherein the analyte is glycated hemoglobin (hemoglobin A1c).

12. The cartridge of claim 1, wherein the affinity medium comprises a polymer comprising a binding moiety.

13. The cartridge of claim 12, wherein the polymer is cross-linked.

14. The cartridge of claim 12, wherein the polymer comprises agarose.

15. The cartridge of claim 12, wherein the polymer comprising a binding moiety is a reaction product of a polymer and a boronic acid or its derivative.

16. The cartridge of claim 15, wherein the polymer further comprises a spacer or an activator.

17. A system comprising the cartridge of claim 1, wherein the system is configured to measure the amount of the analyte.

18. The system of claim 17, wherein the system further comprises a spectrometer.

* * * * *